United States Patent [19]

Naujokas et al.

[11] Patent Number: 5,051,528

[45] Date of Patent: Sep. 24, 1991

[54] RECOVERY PROCESS FOR ETHYLENE GLYCOL AND DIMETHYLTEREPHTHALATE

[75] Inventors: Andrius A. Naujokas, Webster; Kevin M. Ryan, Brockport, both of N.Y.

[73] Assignee: Eastman Kodak Company, Rochester, N.Y.

[21] Appl. No.: 521,070

[22] Filed: Apr. 24, 1990

[51] Int. Cl.$^5$ .................... C07C 67/60; C07C 27/26
[52] U.S. Cl. ...................... 560/78; 562/483; 562/485; 568/854
[58] Field of Search ............... 560/78; 562/483, 485; 568/854

[56] References Cited

U.S. PATENT DOCUMENTS

| | | | |
|---|---|---|---|
| 3,037,050 | 5/1962 | Helsenberg | 560/78 |
| 3,321,510 | 5/1967 | Lotz et al. | 560/78 |
| 3,488,298 | 1/1970 | Barkey et al. | 560/78 |
| 3,701,741 | 10/1972 | Meyer et al. | 560/78 |
| 3,776,945 | 12/1973 | Ligorati | 560/78 |
| 4,163,860 | 8/1979 | Delattre et al. | 560/96 |
| 4,578,502 | 3/1986 | Cudmore | 560/79 |

Primary Examiner—Jose G. Dees
Assistant Examiner—Vera C. Clarke
Attorney, Agent, or Firm—Robert A. Gerlach

[57] ABSTRACT

A method of recovering ethylene glycol and dimethyl terephthalate from scrap polyethylene terephthalate resins by dissolving the scrap in oligomers of the same monomers and passing methanol through the solution.

5 Claims, 1 Drawing Sheet

RECOVERY PROCESS FOR ETHYLENE GLYCOL AND DIMETHYLTEREPHTHALATE

BACKGROUND OF THE INVENTION

1. Field of the Invention

This invention relates to the recovery of ethylene gylcol and dimethylterephthalate from scrap polyethylene terephthalate polyesters. More particularly, it relates to a simplified method of obtaining the constituent monomers of polyethylene terephthalate from scrap wherein the process is practiced under atmospheric conditions without deterioration of the yields.

2. Description of Related Art

Various methods have been disclosed heretofore for the recovery of ethylene glycol and terephthalic acid or derivatives thereof.

U.S. Pat. No 3,776,945 teaches a process of depolymerizing polyethylene terephthalate waste to obtain dimethylterephthalate and ethylene glycol by subdividing the waste into dimensions between 4 and 35 mesh and treating at a temperature of 100° C. to 300° C. and a pressure from 1 to 150 atmospheres with methanol in a quantity that the proportion of methanol to waste is between 1:1 and 10:1 by weight in the presence of acid catalysts.

U.S. Pat. No. 3,321,510 relates to a process of decomposing polyethyleneterephthalate by first treating with steam at a temperature of from about 200° C. to 450° C. and then reducing the steam-treated polyethyleneterephthalate in the form of a brittle solid product to a powder having a mean particles size of from about 0.0005 to 0.002 millimeters and subsequently atomizing the fine powder with a gaseous substance including inert gas and methanol vapor to form an aerosol which is conducted through a reaction zone at a temperature of 250° C. to 300° C. in the presence of excess methanol vapors.

U.S. Pat. No. 3,037,050 relates to the recovery of terephthalate acid dimethyl ester by treating polyethyleneterephthalate in the form of bulky or lumpy solid masses with super-heated methanol vapor in the presence of any suitable esterification catalyst substantially at atmospheric pressure.

U.S. Pat. No. 4,578,502 relates to a procedure for recovering monomeric polycarboxylic acids and polyols from solid scrap polyesters by granulating the scrap resin, slurring the resin with sufficient solvents such as water or methanol, depolymerizing the slurried resin by the application of heat and pressure for a time sufficient to convert substantially all of the resin into its monomeric components, crystallizing the monomeric polycarboxylic acid present by flash crystallization and recovering the polycarboxylic acid and then the polyol by distillation.

U.S Pat. No. 4,163,860 relates to a process for converting a bis-(diol) terephthalate to dimethylterephthalate by interchange in a substantially anhydrous methanol medium in the presence of a magnesium methylate catalyst.

U.S. Pat. No. 3,701,741 relates to a method of recovering substantially pure poly(ethyleneterephthalate) from scrape poly(ethyleneterephthalate) contaminated with impurities by dissolving the contaminated material at elevated temperatures and super-atmospheric pressure in a volatile solvent. This patent does not relate to the recovery of the monomeric ingredients that comprise the polymer.

U.S. Pat. No. 3,488,298 relates to a process for recovering dimethylterephthalate and ethylene glycol from poly(ethyleneterephthalate) scrap by forming a mixture comprising the poly(ethyleneterephthalate) scrape, catalyst and methanol, heating the mixture to approach equilibrium, treating the partially hydrolyzed mixture with an excess of phosphorus-containing compound, heating the treated mixture to fractionate the constituents and recovering methanol, ethylene glycol and dimethylterephthalate.

It can be seen from the above-recited art that many different techniques have been employed in the recovery of the monomeric constituents from poly(ethyleneterephthalate) resins.

These resins have found wide spread use in many and varied applications. For example, poly(ethyleneterephthalate) polyester resins find applications in the preparation of many types of films, including photographic film base, in fibers and in the preparation of food containers such as bottles and the like. Thus, there is a widespread need for a simple and economical method of treating such polyesters to recover the initial ingredients utilized in the preparation of the polyester polymers.

SUMMARY OF THE INVENTION

The invention provides an improved atmospheric pressure method of recovering ethylene glycol and dimethylterephthalate from polyethyleneterephthalate scrap resins by dissolving the scrap polyester resin oligomers of the same monomers as present in the scrap, passing super-heated methanol through the solution and recovering the ethylene glycol and dimethylterephthalate. The process is also advantageous in that the recovered dimethylterephthalate and ethylene glycol is freed of impurities by this method. Thus, the make up of the scrap polyester from which the constituents are recovered need not be considered prior to the recovery procedure and the inventive method is very satisfactory. For example, the following scrap sources are available even if they contain large amounts of impurities:

(1) ground bottle scrap including all the components present, such as, bottle contents, bottle caps, labels and polyethylene bottom cups;

(2) subbed film scrap;

(3) photographic film;

(4) washed film scrap;

(5) still dregs from polyester recovery plant; and (6) scrap polyester containing polymers including acetate resins, polyvinyl chloride and the like. By oligomers of the same monomers is meant, that the monomers which form constituent parts of the oligomer are the same as that of the polymer, i.e., ethylene gylcol and terephthalic acid or dimethylterephthalate. In accordance with Grant and Hacks Chemical Dictionary, Fifth Edition, published by MaGraw-Hill Book Company, an oligomer is "a polymer whose properties change with the addition or removal of one or a few repeating units. The properties of a true polymer do not change markedly with such modification". In accordance with this invention an oligomer is any low molecular weight polyester polymer of the same constituency as that of the scrap material being employed as the starting component wherein the scrap polymer will dissolve in the low molecular weight oligomer. The constituent units of the oligomer used in accordance with this invention will repeat "n" times wherein the "n" will vary between 2 and 100 and a molecular range of between 384 and 19200. In this oligomer composition, many polymer units of varying chain links is present. Values of n as low as 2 to 5 or as high as 50 to 100 are suitable in accordance with this invention.

DESCRIPTION OF PREFERRED EMBODIMENTS

Figure 1:
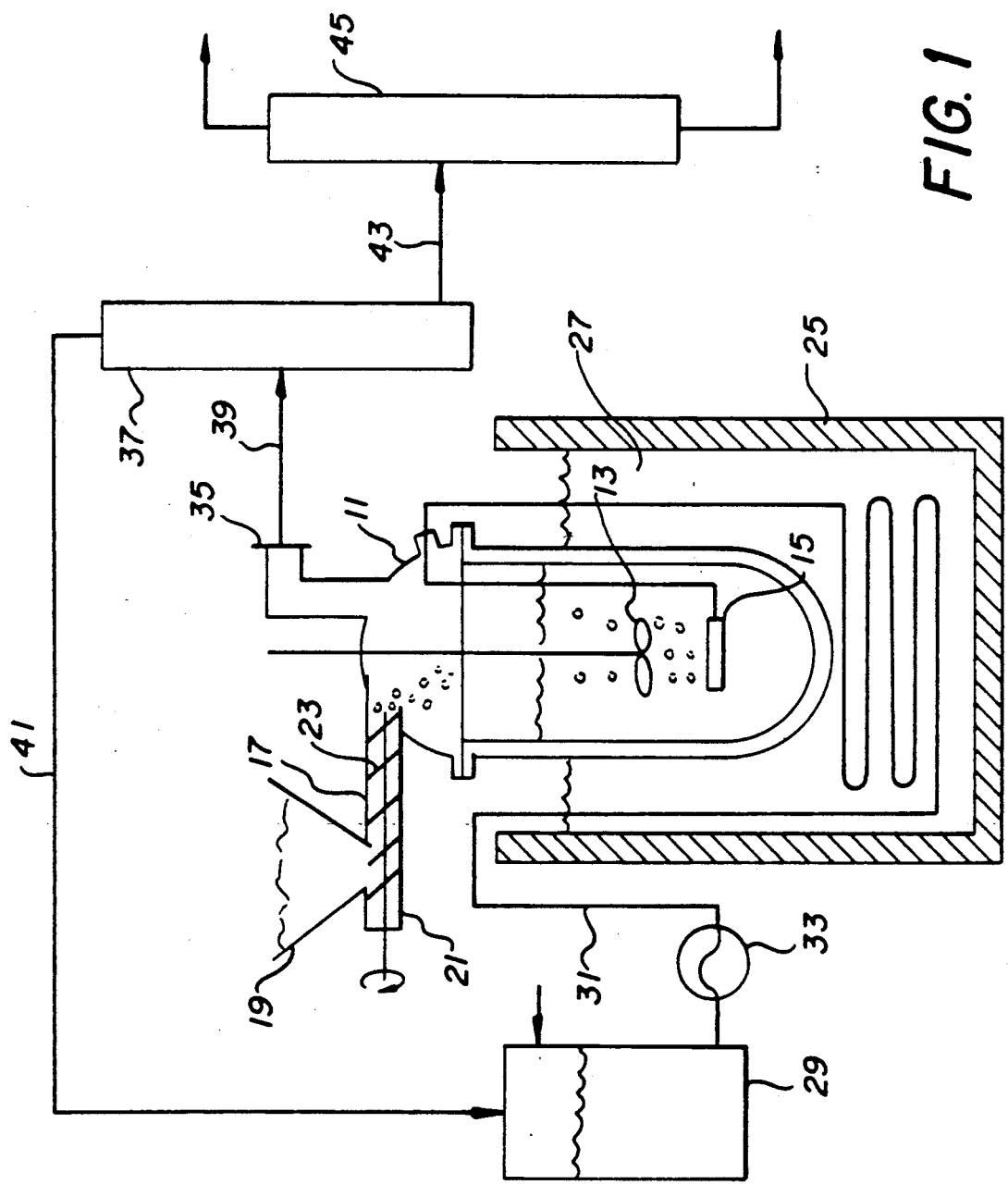
FIG. 1 is a schematic flow diagram illustrating an apparatus suitable for use in practicing the process of this invention.

FIG. 1 illustrates in diagrammatic fashion a flow chart for practicing the process in accordance with this invention. Reactor 11 is equipped with an agitator 13 driven by a motor (not shown), a temperature sensing means (now shown), a sparging means 15 for introducing a gas into the reactor 11 and a scrap introduction means 17 made up of hopper 19, barrel 21 and auger 23. The auger is provided with a motor means (not shown) for rotating the auger 23 within barrel 21. The reactor 11 is provided with a means for controlling the temperature of the contents thereof. While any suitable control means may be employed, FIG. 1 depicts a container 25 having contents 27 which can be maintained at a suitable constant temperature by an external heating means (not shown). The contents 27 may be a salt bath for example. Container 25 is provided with a means (not shown) for raising and lowering in order that reactor 11 can be positioned relative with respect to the contents 27 of container 25. A reservoir 29 is connected by means of conduit 31 with sparging means 15. Conduit 31 has disposed therein pump 33 for delivering the contents of reservoir 29 to sparging means 15 via conduit 31. Conduit 31 has associated therewith a heating means which in the case as shown is a length of conduit 31 doubled upon itself and disposed within heating medium 27 in container 25. Reactor 11 is further provided with outlet means 35 connected to first distillation device 37 by conduit 39. Conduit 41 is provided to return the overheads from distillation device 37 to reservoir 29. Conduit 43 conveys the higher boilers to second distillation device 45.

In operation, oligomers of dimethylterephthalate and ethylene glycol are introduced into reactor 11 to at least approximately 50% of the volume of the reactor 11 and agitator 13 and heating means depicted as container 25 and contents thereof 27 actuated to bring the temperature of the oligomers to from about 220° C. to about 270° C. Scrap feeding means 17 loaded with polyethyleneterephthalate scrap resin is actuated to deliver scrap resin to the contents of reactor 11. Pump 33 is actuated to deliver methanol from reservoir 29 through conduit 31 wherein the methanol is super-heated and delivered through sparging means 15 into the contents of reactor 11 as a vapor which passes through the solution of the polyethyleneterephthalate and the oligomer thereof. The methanol is recovered by passing out through outlet 35 through conduit 39 and distillation device 37 back through conduit 41 to the methanol reservoir 29. The recovered dimethylterephthalate and ethylene glycol also exits via outlet 35 through conduit 39, are separated from the methanol in distilling device 37 and past via conduit 43 to second distillation device 45 where the ethylene glycol is collected overhead while the dimethylterephthalate is removed below. It may be desirable for conduit 39 to be provided with a heating means in order to prevent the condensation of any of the three components exiting from reactor 11.

It is, of course, to be understood while the process described above is semi-continuous in nature, that the method in accordance with this invention may be carried out as a batch, a semi-continuous or continuous method. In the semi-continuous method depicted above, which involves the feeding of polyester scrap into the reactor at a rate substantially equivalent to product formation, impurities will accumulate in reactor 11 necessitating periodic clean out. In a continuous mode of operating the process in accordance with this invention for example, a small slip stream of the reactor contents would continuously be removed, the rate being based on the rate of impurities being introduced into the reactor. An advantage associated with all of the three techniques, whether it be batch, semi-continuous or continuous, is that any catalyst employed in the preparation of the virgin poly(ethyleneterephthalate) resin will not enter the product vapor stream but will be removed along with the impurities due to the low volatility of these catalysts.

The invention will be illustrated by the following examples in which parts are by weight unless otherwise specified:

EXAMPLE 1

A reactor 11 is charged with 2000 parts of polyethylene terephthalate oligomers containing a mixture having between 10 and 20 repeating units heated to about 250° C. to render the mass molten. Clean polyethylene terephthalate powder is fed by means 17 at the rate of 3.5 parts/minute and methanol is feed at the rate of 20 part by volume and sparged through the molten resin by means 15. The methanol is returned to reservoir 29 via distillation column 37 and conduit 41. The dimethyl terephthalate and ethylene glycol are recovered from distillation column 45.

EXAMPLE 2

A reactor similar to that of Example 1 is charged with about 630 parts of the oligomer mixture of Example 1 heated to about 225° C. to render it molten. Methanol is feed to the sparging means 15 at a rate of 4 parts by volume/minute and ground scrap polyethylene terephthalate bottles including polyolefin bottom cups, aluminum bottle caps, labels and any adherents used for the labels and bottom caps are fed to the reactor at a rate of 2.5 parts/minute. As in Example 1 the methanol is returned to reservoir 29 and the ethylene glycol and dimethyl terephthalate recovered from distillation column 45. Crystalline dimethyl terephthalate with a light layer of polyolefins and aluminum collecting at the bottom of the melt are removed from the reactor.

What is claimed is:

1. A method of recovering ethylene glycol and dimethylterephthalate from polyethyleneterephthalate polyesters which comprises dissolving scrap polyester in oligomers of ethylene glycol and terephthalic acid or dimethyl terephthalate, passing super-heated methanol through the solution and recovering the ethylene glycol and dimethylterephthalate.

2. The method of claim 1 wherein the process is conducted under atmospheric pressure.

3. The process of claim 1 wherein the scrap is heated to a temperature of from about 20° to 270° C. during the contact with methanol.

4. The method of claim 1 wherein an excess quantity of methanol is passed through the solution.

5. The method of claim 1 wherein the ethylene glycol and dimethylterephthalate are recovered by distillation.

* * * * *